United States Patent [19]

Mazurek et al.

[11] Patent Number: 4,788,376
[45] Date of Patent: Nov. 29, 1988

[54] PROCESS FOR PRODUCING HIGHER HYDROCARBONS FROM LOWER OLEFINS

[75] Inventors: Harry Mazurek, Bala Cynwyd; John A. Sofranko, West Chester, both of Pa.

[73] Assignee: Atlantic Richfield Company, Los Angeles, Calif.

[21] Appl. No.: 84,720

[22] Filed: Aug. 13, 1987

[51] Int. Cl.$^4$ .............................................. C07C 2/12
[52] U.S. Cl. .................................... 585/533; 585/361; 585/646; 585/647
[58] Field of Search ............... 585/533, 260, 262, 361, 585/646, 647

[56] References Cited

U.S. PATENT DOCUMENTS

| | | | |
|---|---|---|---|
| 3,404,101 | 10/1968 | Welsang | 585/260 |
| 3,546,313 | 12/1970 | Banks | 585/647 |
| 3,658,927 | 4/1972 | Crain | 585/647 |
| 3,660,507 | 5/1972 | Reusser | 585/647 |
| 3,689,589 | 9/1972 | Reusser | 585/646 |
| 3,717,586 | 2/1973 | Suggitt | 585/533 |
| 3,804,917 | 4/1974 | Shepard | 585/533 |
| 3,897,508 | 7/1975 | Thatchenko | 585/361 |
| 4,454,368 | 6/1984 | Banks | 585/647 |
| 4,665,247 | 5/1987 | Dessau | 585/361 |

*Primary Examiner*—Asok Pal
*Attorney, Agent, or Firm*—William C. Long

[57] ABSTRACT

The process of the invention comprises contacting a lower olefin contaminated with an impurity such as a diene at oligomerization conditions with either a mixture of oligomerization catalyst and at least one of a methathesis catalyst and an alkaline earth oxide, or precontacting the contaminated lower olefin with methathesis catalyst, optionally combined with alkaline earth oxide, and subsequently oligomerizing the lower olefin.

12 Claims, 4 Drawing Sheets

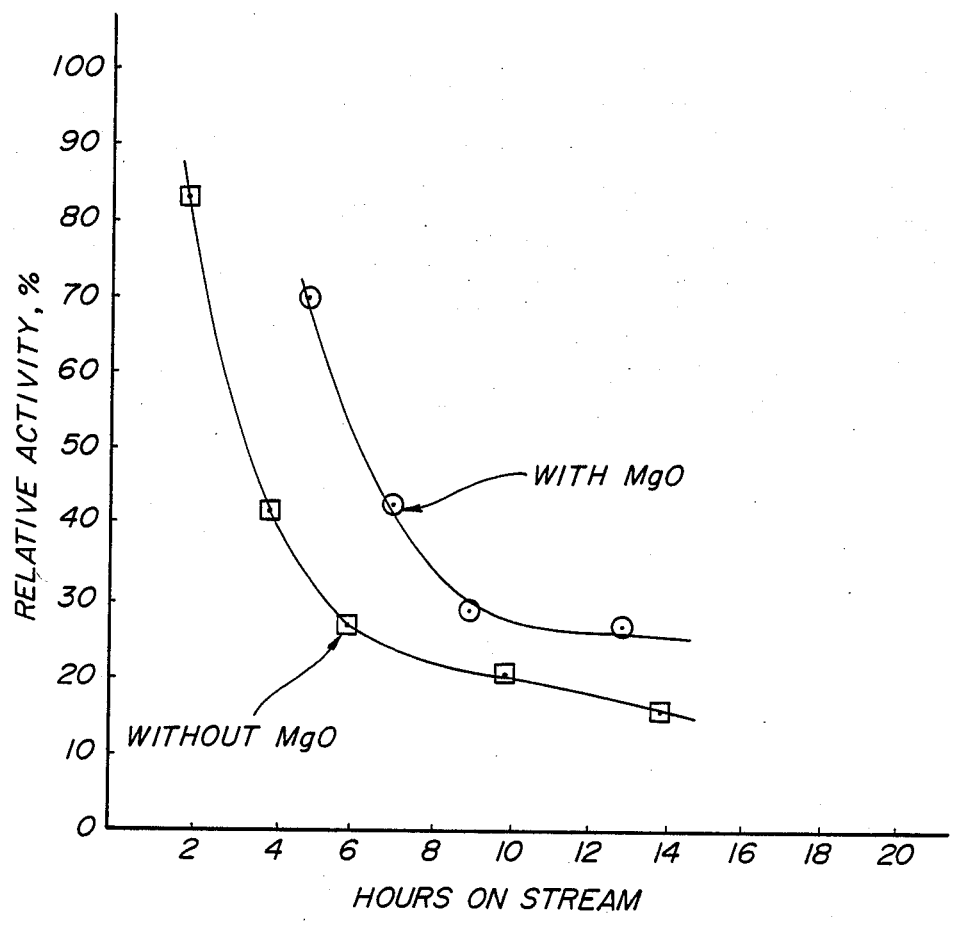

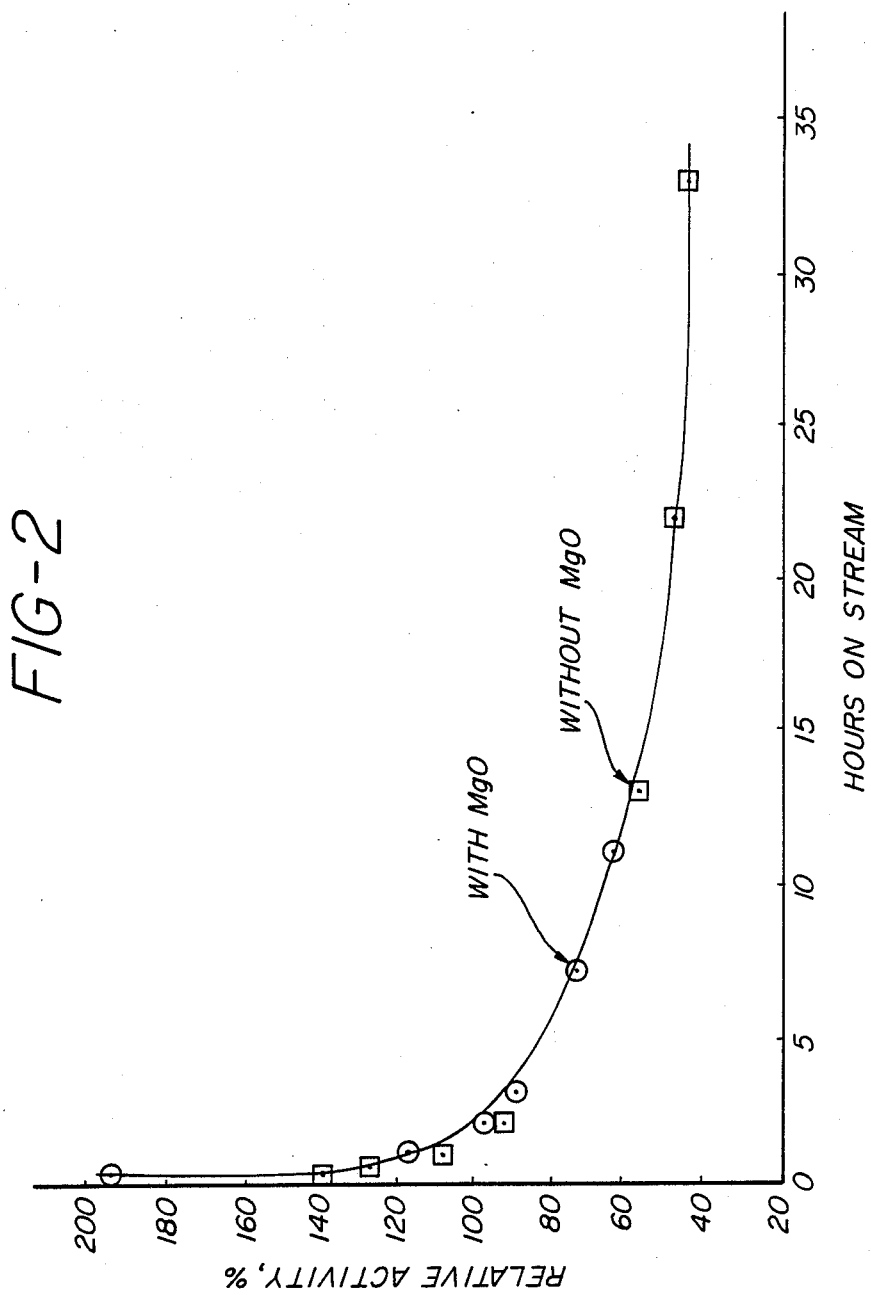

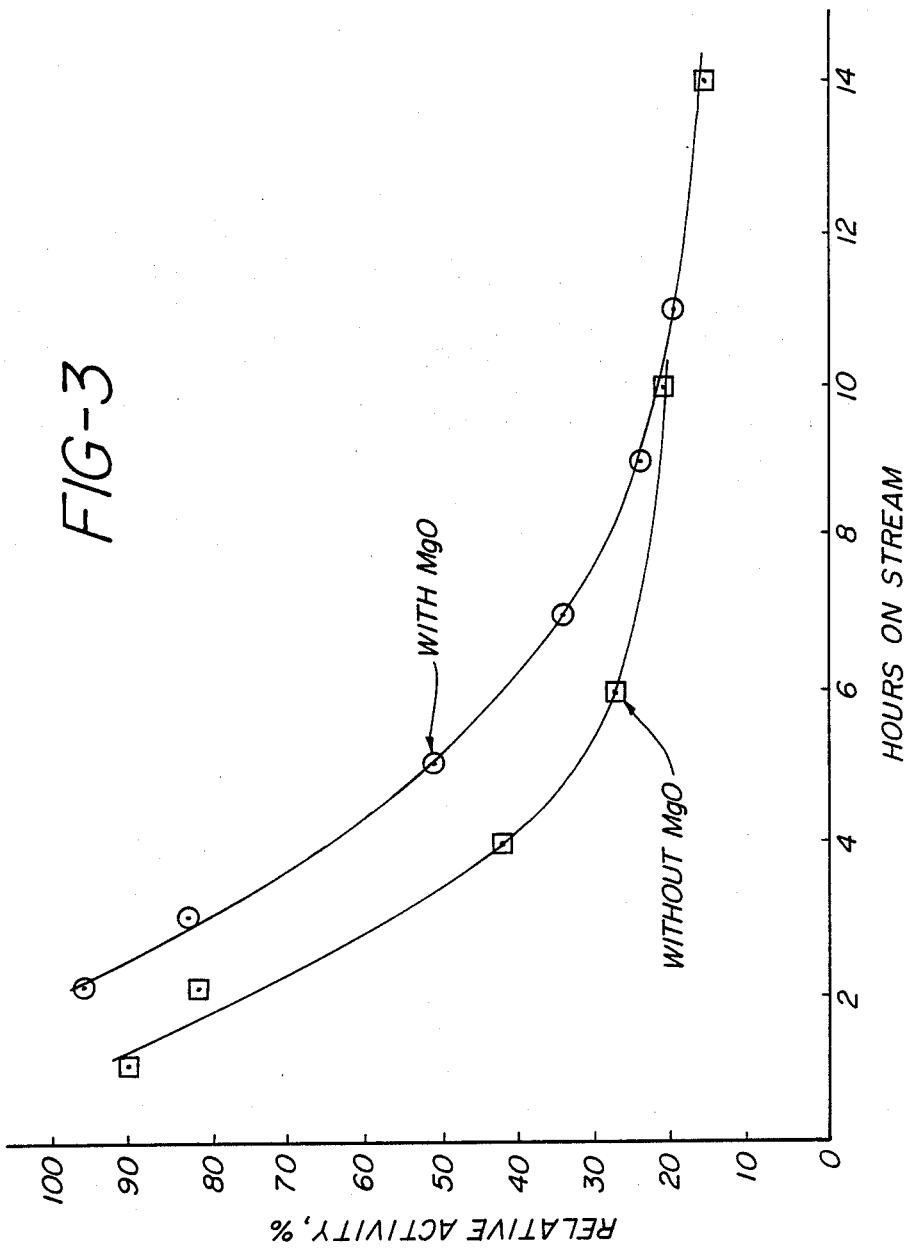

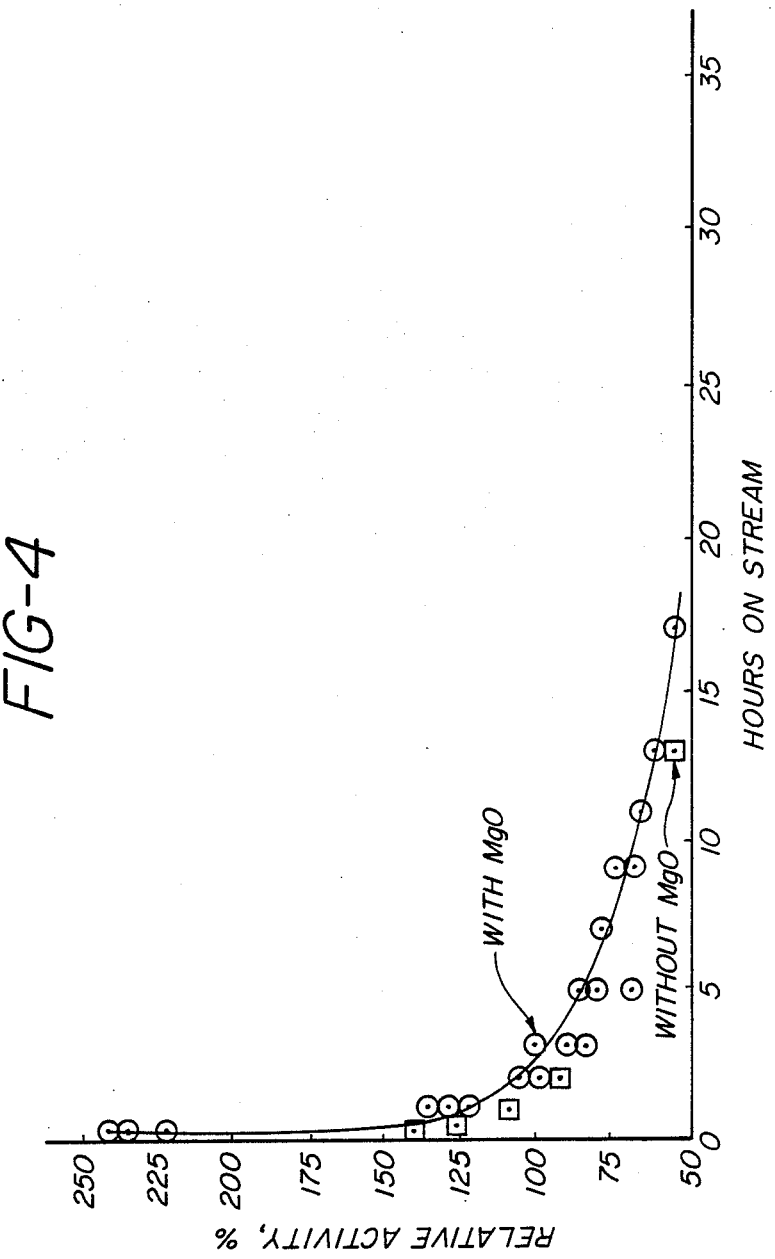

PROCESS FOR PRODUCING HIGHER HYDROCARBONS FROM LOWER OLEFINS

BACKGROUND OF THE INVENTION

This invention relates to an improved process for the production of higher hydrocarbons from lower olefins. More particularly, the invention relates to a process for producing higher hydrocarbons from a lower olefin feedstock also containing a contaminant such as butadiene which tends to deactivate oligomerization catalysts.

Converting lower olefins, such as ethylene, propylene, butylene and mixtures thereof, to higher hydrocarbons has been widely used, for example, to produce polymer gasoline. Recently, some work has been directed toward olefin oligomerization to produce higher hydrocarbons from lower olefins derived from methane conversion. See U.S. Pat. No. 4,556,749; and commonly assigned U.S. patent application Ser. Nos. 06/728,060 filed 4/29/85, 06/730,886 filed 4/30/85, and 06/817,853 filed 12/16/85.

Quite often the lower olefin-containing feedstocks also include minor amounts of impurities such as conjugated dienes, e.g., 1,3 butadiene, as well as allenes and acetylenes, which may be produced as a by-product of the lower olefin production process. This is particularly the case where the lower olefin is produced by pyrolysis of hydrocarbons, e.g., natural gas liquid, naphtha and gas oil, or by methane conversion, especialy methane conversion processes involving methane/solids contacting at elevated temperature to produce higher hydrocarbons (e.g., lower olefins) and coproduct water.

The presence of impurities such as conjugated dienes and the like is often detrimental to catalysts used to oligomerize lower olefins to higher hydrocarbons. Conventional diene removal steps, such as distillation, selective diene hydrogenation and the like, are costly and can cause loss of the lower olefin. Still, it would be beneficial to remove impurities from the lower olefin feedstock and/or reduce the harmful effect that these impurities have on lower olefin oligomerization catalysts.

Therefore, one object of the present invention is to provide an improved process for converting a lower olefin feedstock containing oligomerization catalyst deactivating impurities to higher hydrocarbons. Another object of the invention is to provide a process in which dienes are effectively removed from a lower olefin, diene-containing feedstock. A further object of the invention is to provide a process in which the detrimental effect on an olefin oligomerization catalyst of dienes in a lower olefin, diene-containing feed is substantially reduced.

SUMMARY OF THE INVENTION

In accordance with the present invention, a process is provided whereby a lower olefin, containing a contaminant which tends to deactivate olefin oligomerization catalysts, can be converted to higher hydrocarbons. Specifically, the process of the invention comprises either contacting the contaminated lower olefin at oligomerization conditions with a mixture of oligomerization catalyst and at least one of a metathesis catalyst and an alkaline earth oxide, or precontacting the contaminated lower olefin at metathesis conditions with metathesis catalyst, optionally combined with alkaline earth oxide, and subsequently oligomerizing the lower olefin.

Through practice of the invention, the contaminants present in the feed are converted to materials which do not tend to deactivate the oligomerization catalyst, and greatly improved lower olefin oligomerization is achieved without the costly separation and purification procedures associated with the prior act.

THE DRAWINGS

FIGS. 1-4 graphically show catalyst activity as a function of hours on stream for Examples 6-10.

DETAILED DESCRIPTION OF THE INVENTION

The lower olefin created by the invention is selected from the group consisting of ethylene, propylene, butylene and mixtures thereof. Preferably ethylene, propylene and mixtures thereof are treated. Still more preferably, a major portion of the lower olefin component comprises ethylene. The oligomerization deactivating agent typically comprises one or more dienes which are produced as a by-product with the lower olefin. In particular, the diene component is a conjugated diene, usually 1,3 butadiene. Other contaminants include methyl acetylene, and the like. The composition of the feed to the process of the invention can vary widely. Generally the lower olefin content comprises from about 5% to about 100%, more preferably from about 10% to about 100%, by weight of the feedstock. The contaminating component is typically present in the feedstock in a relatively minor amount relative to the amount of lower olefin component present. Usually, the contaminant is present in an amount in the range of about 1 ppm to about 1%, more preferably about 10 ppm to about 1000 ppm, by weight of the feedstock.

In certain situations, e.g., when the feedstock is derived from the above-noted methane conversion processes, the feedstock further comprises a major amount, i.e., at least about 50% by weight, of alkane. This alkane component, preferably selected from the group consisting of methane, ethane, propane, butane and mixtures thereof, more preferably methane, ethane and mixtures thereof, does not typically become involved in the conversion of either of the lower olefin component or the contaminant, and may be considered a diluent in the feedstock. Other diluents such as carbon oxides and steam may also be present. If the alkane component is present, it may be present in the feedstock in amounts of about 80% or more by weight of the feedstock.

Several different embodiments of the invention can be practised. In a first, preferred embodiment there is formed an admixture of an olefin oligomerization catalyst and either or both a metathesis catalyst and an alkaline earth oxide, and the contaminated lower olefin is passed over the catalyst mixture at oligomerization conditions. It has surprisingly been found that deactivation of the oligomerization catalyst is significantly reduced through the use of such mixtures.

In a quite separate embodiment, the contaminated lower olefin is first passed through a "guard bed" of metathesis catalyst which optionally may also contain alkaline earth oxide, and then through the bed containing the oligomerization catalyst. Essentially the same reaction conditions can be maintained in each bed.

Through practice of the invention, the deleterious effects of the oligomerization catalyst deactivation contaminant, e.g., butadiene, are substantially avoided.

Effective life of the oligomerization catalyst is greatly extended and thus the production of higher hydrocarbons from the lower olefin is substantially improved.

Catalysts which are active for the metathesis of olefins, including dienes, and which are used in the process of this invention are of a generally known type. In this regard, reference is made to "Journal of Molecular Catalysis", 28 (1985) pages 117-131, to "Journal of Catalysis", 13 (1969) pages 99-113, to "Applied Catalysis" 10 (1984) pages 219-229 and to "Catalysis Reviews", 3 (1) (1969) pages 37-60.

Such catalysts may be homogeneous or heterogeneous, with heterogeneous catalysts being preferred. The catalyst preferable comprises a catalytically effective amount of a transition metal component. The preferred transition metals for use in the present invention include tungsten, molybdenum, nickel, rhenium and mixtures thereof. The transition metal component may be present as elemental metal and/or one or more compounds of the metal. If the catalyst is heterogenous, it is preferred that the transition metal component be associated with a support. Any suitable support material may be employed provided that it does not substantially detrimentally interfere with the feedstock components, the diene component conversion, the lower olefin component conversion, or the oligomerization catalyst. Preferably, the support material is an oxide, such as silica, alumina, titania, zirconia and mixtures thereof. Silica is a particularly preferred support material. If a support material is employed, the amount of transition metal component used in combination with the support material may vary widely depending, for example, on the particular application involved and/or the transition metal being used. Preferably, the transition metal comprises about 0.1% to about 30%, more preferably about 1% to about 20%, by weight (calculated as elemental metal) of the total first catalyst.

The metathesis catalysts advantageously comprise a catalytically effective amount of at least one of the above-noted transition metals, and are capable of promoting diene metathesis. This is especially advantageous because one of the products of this reaction is a lower olefin. To illustrate this, butadiene metathesis produces one molecule of ethylene and one $C_6$ molecule which ultimately may be cyclic in nature. Not only is the diene component converted, but the diene metathesis reaction also produces additional lower olefin component.

Preferably, the metathesis catalyst further comprises at least one activating agent present in an amount to improve the effectiveness of the catalyst. Various activating agents may be employed, including activating agents which are well known in the art to facilitate metathesis reactions. Preferred activating agents include organo-metallic compounds, such as tetra methyl tin, oxides, such as alkaline earth metal oxides, alumina and silica, and mixtures thereof. In one particular embodiment, when the activating agent is at least one oxide, the activating agent may be used as a support for the transition metal component. If an organo-metallic activating agent is employed the agent may be included with the catalyst during catalyst preparation, or it may be added during reaction. Preferably, the amount of organo-metallic activating agent is relatively minor compared to the amount of catalytically active metal component in the first catalyst.

It has been found that alkaline earth metal components are not only good activating agents for transition metal catalysts, but when used in admixture with oligomerization catalyst serve to greatly enhance the life of the oligomerization catalyst even in the absence of metathesis catalyst. The alkaline earth metals include magnesium, calcium, barium and strontium. Oxides of magnesium, calcium, barium and mixtures thereof, particularly magnesia, are preferred. The amount of alkaline earth metal component present in a catalyst may vary widely. Preferably alkaline earth metal is present in amount of about 1% to about 100%, more preferably from about 5% to about 100%, and still more preferably about 20% to about 100%, by weight (calculated as alkaline earth metal oxide) of the total of alkaline earth metal and metathesis catalyst when used in admixture with oligomerization catalyst.

The catalyst may be prepared using any one or a combination of conventional catalyst preparation techniques. Therefore, it is not necessary to present a detailed description of the catalyst preparation techniques here. To illustrate the many possible approaches to first catalyst preparation, if the catalyst is to be heterogeneous, i.e., a solid, and contain at least one transition metal component, the transition metal component, or a precursor of such component, can be combined with the support by precipitation, co-precipitation, impregnation, ion exchange and the like well known procedures. The transition metal component/support combination is preferably dried and calcined prior to being used.

Numerous catalysts and processes are known for the conversion, e.g., oligomerization, of olefins generally, and of ethylene particularly. For example, phosphoric acid supported on a kieselguhr base has been widely used for making polymer gasoline, i.e., olefinic hydrocarbon liquids within the gasoline boiling range, from refinery gases. Other catalysts which have been employed for similar purposes include the oxides of cobalt, nickel, chromium, molybdenum and tungsten on supports such as alumina, silica-alumina, kieselguhr, carbon and the like.

Included within the scope of the present invention are all catalysts and processes which are effective for the oligomerization of olefins to higher hydrocarbons, preferably olefinic hydrocarbon liquids within the gasoline boiling range. Without intending to limit the scope of the claimed invention, most oligomerization catalysts may be classified in one of two general categories: metal catalysts and acid catalysts. They may also be classified as heterogeneous (solid) catalysts or homogeneous (liquid-phase) catalysts.

For examples of metal catalysts based on nickel, see U.S. Pat. Nos. 2,828,347; 3,459,826; 3,527,839; 3,954,668; 3,959,400; 4,260,844; 4,272,406; 4,288,648; 4,293,725; and *Industrial Chemistry*, 47 pp. 752, et seq. (1955). Note that these catalysts require a donor ligand and a Lewis acid. For examples of metal catalysts based on palladium, see U.S. Pat. Nos. 3,644,565; 3,728,415; 3,738,977; 3,758,626; and 3,920,763. An example of metal catalysts based on chromium is found in U.S. Pat. No. 3,709,954. An example of metal catalysts based on cobalt is found in *Industrial and Engineering Chemistry*, 42, pp. 2580, et seq. (1950). Examples of metal catalysts based on titanium are found in U.S. Pat. Nos. 3,981,941 and 4,110,410. An example of metal catalysts based on tungsten is found in U.S. Pat. No. 3,903,193. An example of metal catalysts based on rhenium is found in U.S. Pat. No. 3,393,251.

Examples of phosphoric acid catalysts are described in U.S. Pat. Nos. 2,383,318 and 3,887,634 and also in *Industrial and Engineering Chemistry*, 27, pp. 1364, et seq. (1935). Acid catalysts based on chlorided or fluorided alumina are found in U.S. Pat. Nos. 3,364,191 and 3,515,769 and also in USSR Pat. No. 107,176.

Other acid catalysts of particular interest in the context of the present invention are siliceous, crystalline molecular sieves. Such silicon-containing crystalline materials include materials which contain, in addition to silicon, significant amounts of aluminum. These crystalline materials are frequently named "zeolites", i.e., crystalline aluminosilicates. Silicon-containing crystalline materials also include essentially aluminum-free silicates. These crystalline materials are exemplified by crystalline silica polymorphs (e.g., silicate, disclosed in U.S. Pat. No. 4,061,724 and organosilicates, disclosed in U.S. Pat. No. RE 29,948), chromia silicates (e.g., CZM), ferrosilicates and galliosilicates (see U.S. Pat. No. 4,238,318), and borosilicates (see U.S. Pat. Nos. 4,226,420; 4,269,813; 4,499,325; and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see U.S. Pat. No. 4,016,246). Examples of processes for the conversion of low molecular weight olefins over zeolites are found in U.S. Pat. Nos. 2,972,643; 3,325,465; 3,960,978; 3,972,832; 4,021,502; 4,044,065; 4,150,062; and 4,254,295. Also see U.S. Pat. Nos. 4,417,086 and 4,417,087 wherein oligomerization processes employing fluidized crystalline molecular sieves are disclosed.

In addition to the zeolites described above, other known oligomerization of the ALPO and SAPO type (aluminophosphates and silicoaluminophosphates, e.g. SAPO-5, SAPO-11, etc.) can be used. See for example U.S. Pat. Nos. 4,310,440; 4,499,315; 4,499,316; and the like.

Metal oligomerization catalysts in general are more snnsitive to feed impurities, (e.g., water, carbon monoxide, dienes, etc.) than are the acid catalysts, although the acid catalysts can also be sensitive to the presence of such feed impurities. Although homogeneous, metal catalysts are quite active, the need for dry feeds, solvents, and other measures to prevent catalyst deactivation and precipitation is disadvantageous and suggest an obvious advantage to supported, heterogeneous, metal catalyst. Homogeneous acid catalysts are effective but are also corrosive and tend to form two liquid-phase systems with the non-polar hydrocarbon oligomerization products. Considering the foregoing observations, heterogeneous acid catalysts are the preferred catalyst for use in the present invention. Of the heterogeneous acid catalysts, acid zeolites are especially preferred, particularly zeolites of the ZSM-type and borosilicates.

When the oligomerization catalyst is in the form of a solid, preferably an acid solid, the preferred operating parameters of the oligomerization include a temperature in the range of about 100° C. to about 500° C., more preferably about 150° C. to about 370° C.; a pressure in the range of about 0.1 to about 100 atmospheres, more preferably about 1 to about 70 atmospheres; and a space velocity within the range of about 0.1 to about 50, more preferably about 0.2 to about 20, WHSV, based on the amount of lower olefin component present in the feedstock. It should be noted that these reaction conditions are applicable both in the embodiment where a mixture of metathesis catalyst and/or alkaline earth oxide with oligomerization catalyst is used or in both beds where a guard bed containing metathesis catalyst is used before the oligomerization catalyst.

Selection of operating parameters suitable to accomplish any of the foregoing objectives have previously been described in the particular context of oligomerization using ZSM-5 type zeolites. See for example, U.S. Pat. No. 3,760,024 (describes conversion of $C_2$–$C_4$ paraffins and/or olefins); U.S. Pat. No. 3,960,978 (describes conversion of $C_2$–$C_5$ of olefins to a gasoline fraction containing no more than about 20 wt. % aromatics); U.S. Pat. No. 4,021,502 (describes conversion of gaseous olefins to higher molecular weight olefins over ZSM-5, ZSM-12, ZSM-18 chabazite or zeolite beta); and U.S. Pat. No. 4,227,992 (describes selective oligomerization of $C_3+$ olefins to produce fuel oil and gasoline products). The entire content of each of these patents is hereby incorporated by reference herein.

In the event that a physical admixture of metathesis catalyst and/or alkaline earth oxide with oligomerization catalyst is employed, it is preferred that the oligomerization catalyst comprise about 1% to about 80%, more preferably about 5% to about 70%, by weight of the total first and second catalyst present.

The present invention is further illustrated by reference to the following, non-limiting examples.

EXAMPLES 1 AND 2

Two experiments were run to determine the effect of a metathesis catalyst on olefin oligomerization of a feedstock containing both ethylene and 1,3 butadiene. The feedstock used in both experiments had the following composition:

|  | Wt. % |
| --- | --- |
| ethylene | 9.5 |
| 1,3 butadiene | 0.7 |
| methane | balance |

In each of these experiments, a fixed bed of catalyst was employed. Other reaction conditions included:

|  |  |
| --- | --- |
| Temperature, °C. | 350 |
| Pressure, psig | 287 |
| WHSV*, hr.$^{-1}$ | 2.2 |

*based on weight of ZSM-5 present and the weight of ethylene and 1,3 butadiene present in the feedstock.

In Example 1, which is not in accordance with the invention, the catalyst was entirely ZSM-5, a crystalline aluminosilicate which is known to have the capability to promote the oligomerization of ethylene to higher hydrocarbons, e.g., $C_5+$ material. ZSM-5 is also known to be sensitive to contact with 1,3 butadiene. That is, the oligomerization activity of ZSM-5 is detrimentally affected by the presence of 1,3 butadiene in the reaction feedstock.

In Example 2, the catalyst bed was made up of a substantially uniform, physical admixture of the following:

|  | Wt. Parts |
| --- | --- |
| ZSM-5 | 3 |
| 7.8 wt. % $WO_3$ on $SiO_2^{(1)}$ | 1 |

-continued

| | Wt. Parts |
|---|---|
| MgO[2] | 3 |

[1] Derived by impregnating SiO$_2$ particles with a tungsten component in a water solution. The impregnated solid was dried and calcined in air.
[2] From Kaiser Aluminum Company.

Each experiment was run for five hours and periodic product samples were collected and analyzed. Results of these analyses were as follows:

TABLE I

| | EXAMPLE 1 | | EXAMPLE 2 | |
|---|---|---|---|---|
| TIME hr. | Ethylene Conversion % | Selectivity to C$_5$+ % | Ethylene Conversion % | Selectivity to C$_5$+ % |
| 0.25 | 88 | 76 | >99 | 67 |
| 1 | 87 | 73 | >99 | 70 |
| 2 | 82 | 70 | >99 | 72 |
| 3 | — | — | >99 | 73 |
| 4 | 3 | 96 | >99 | 73 |
| 5 | — | — | >99 | 75 |

These results clearly demonstrate certain of the benefits of the present invention. For example, the Example 1 results, using solely ZSM-5 catalyst, indicate that the activity of the olefin oligomerization catalyst continually and dramatically declines after a given time in contact with the ethylene/1,3 butadiene containing feedstock. This is in contrast to Example 2, an embodiment of the present invention. The use of ZSM-5 in combination with WO$_3$/SiO$_2$ and magnesia allows for substantially constant ethylene oligomerization over the time period investigated. The WO$_3$/SiO$_2$ and magnesia act to convert 1,3 butadiene in the feedstock to components which do not substantially detrimentally affect the olefin oligomerization catalytic performance of the ZSM-5. This approach to converting dienes is substantially more simple, easy to operate and economical relative to many other schemes, e.g., distillation, selective hydrogenation and the like, to remove dienes from the feedstock.

EXAMPLES 3-5

Comparative runs were made using a dilute ethylene feedstock comprised of about 90% by weight methane, about 9.4% by weight ethylene, and about 0.6% by weight butadiene. Reaction conditions were 350° C., 287 psia and 2 second contact time.

In Example 3 which is not in accordance with the invention a contact bed containing 5 cc of ZSM-5 was employed. The ZSM-5 contained 20% by weight Al$_2$O$_3$ binder.

In Example 4 dual catalyst beds were used, the first "guard bed" comprised of 2.5 cc of 22% by weight Re$_2$O$_7$ on gamma alumina followed by a bed containing 2.5 cc of ZSM-5 which contained 20% by weight Al$_2$O$_3$ binder.

In Example 5 a bed containing an intimate mixture of 2.5 cc of ZSM-5 which contained 20% by weight Al$_2$O$_3$ binder and 2.5 cc of 22% by weight Re$_2$O$_7$ on gamma alumina was employed.

The following table shows the results obtained:

TABLE II

| | Example 3 | | Example 4 | | Example 5 | |
|---|---|---|---|---|---|---|
| TIME hr | Eth Conv. % | Sel to C$_5$+ % | Eth Conv. % | Sel to C$_5$+ % | Eth Conv. % | Sel to C$_5$+ % |
| 0.25 | 96 | 67 | 92 | 62 | 90 | 60 |
| 1 | 95 | 68 | >99 | 68 | >99 | 68 |
| 2 | 94 | 63 | >99 | 68 | >99 | 70 |
| 4 | 93 | 69 | >99 | 67 | >99 | 76 |
| 5 | 92 | 70 | >99 | 68 | >99 | 74 |

EXAMPLES 6-10

A series of runs were made with admixtures of ZSM-5 and MgO in order to demonstrate the beneficial effect of the MgO on oligomerization life where the olefin feed contained butadiene contaminant. Comparisons were made with ZSM-5 containing no MgO for feeds containing butadiene and for feeds containing no butadiene.

Specifically, comparison runs were made at 600°-625° F. and 300 psia with a feed of 90.5% methane, 9.2% ethylene and 0.3% butadiene between ZSM-5 with 20% Al$_2$O$_3$ binder alone and 8 parts ZSM-5 with 20% Al$_2$O$_3$ binder in admixture with 1 part MgO.

FIG. 1 clearly shows the improved results obtained with the ZSM-5/MgO mixed catalyst.

By way of comparison, similar runs were made but with a feed of 90.5% methane and 9.5% ethylene (no butadiene). As seen in FIG. 2, results achieved with the two catalysts were indistinguishable thus illustrating the beneficial results surprisingly achieved with butadiene-containing feed. It can be noted from a comparison of FIG. 1 and FIG. 2 that the ZSM-5 activity declines at a much slower rate where the feed does not contain butadiene.

Similarly, comparison runs were made at 600°-625° F. and 300 psia with a feed of 90.5% methane, 9.2% ethylene, and 0.3% butadiene with a mixed catalyst of 6 parts by weight ZSM-5 containing 20% by weight alumina and 1 part by weight MgO and with just the ZSM-5 containing 20% by weight alumina.

FIG. 3 shows the improved results obtained with the mixed catalyst.

Where no butadiene was contained in the feed under the same conditions the catalyst performances were indistinguishable as shown in FIG. 4.

Each of the accompanying drawings shows relative activity of the particular catalyst system as a function of run time. The relative activity is determined from the ratio of the actual space velocity divided by the space velocity necessary to produce the same conversion using a freshly regenerated catalyst. See DOE Report FE-1773 under U.S. Government Contract No. E(4-9-18)-1773 for the relationship between conversion and space velocity for the standard catalyst.

We claim:
1. In a process for the oligomerization of a lower olefin contaminated with a minor amount of a diene or methyl acetylene oligomerization catalyst deactivating agent, the improvement which comprises
   (a) contacting the contaminated lower olefin with an admixture of zeolitic oligomerization catalyst and at least one of a metathesis catalyst and an alkaline earth oxide at oligomerization conditions, or
   (b) contacting the contaminated lower olefin with a metathesis catalyst at metathesis conditions and thereafter contacting the olefin with a zeolitic oligomerization catalyst at oligomerization conditions.

2. In a process for the oligomerization of a lower olefin contaminated with a minor amount of a conjugated diene oligomerization catalyst deactivating agent, the improvement which comprises contacting the contaminated lower olefin with an admixture of a zeolitic oligomerization catalyst and at least one of a transition metal metathesis catalyst and an alkaline earth oxide at oligomerization conditions.

3. In a process for the oligomerization of a lower olefin contaminated with a minor amount of a conjugated diene oligomerization catalyst deactivating agent, the improvement which comprises contacting the contaminated lower olefin with a transition metal metathesis catalyst and thereafter contacting the olefin with a zeolitic oligomerization catalyst at oligomerization conditions.

4. In a process for the oligomerization of a feedstock containing ethylene and contaminated with 1 ppm to about 1% by weight of 1,3 butadiene, the improvement which comprises contacting said feedstock at 150° to 370° C. and 1 to 70 atmospheres pressure with (a) an admixture of a zeolitic oligomerization catalyst and at least one of a transition metal metathesis catalyst and an alkaline earth oxide, or (b) a transition metal metathesis catalyst and thereafter with a zeolitic oligomerization catalyst.

5. The method of claim 4 wherein the said zeolitic catalyst is ZSM-5.

6. The method of claim 4 wherein the transition metal is rhenium.

7. The method of claim 4 wherein the transition metal is tungsten.

8. The method of claim 4 wherein the alkaline earth oxide is magnesium oxide.

9. The method of claim 4 wherein the feedstock comprises a major proportion of methane.

10. The method of claim 1 further comprising that said metathesis catalyst of (b) is admixed with an alkaline earth oxide.

11. The method of claim 3 further comprising that said metathesis catalyst is admixed with an alkaline earth oxide.

12. The method of claim 4 further comprising that said transition metal metathesis catalyst of (b) is admixed with an alkaline earth oxide.

* * * * *